(12) United States Patent
Koll et al.

(10) Patent No.: US 11,922,373 B2
(45) Date of Patent: *Mar. 5, 2024

(54) CLINICAL DATA RECONCILIATION AS PART OF A REPORT GENERATION SOLUTION

(71) Applicant: 3M INNOVATIVE PROPERTIES COMPANY, St. Paul, MN (US)

(72) Inventors: Detlef Koll, Pittsburgh, PA (US); Juergen Fritsch, Pittsburgh, PA (US)

(*) Notice: Subject to any disclaimer, the term of this patent is extended or adjusted under 35 U.S.C. 154(b) by 108 days.

This patent is subject to a terminal disclaimer.

(21) Appl. No.: 17/579,975

(22) Filed: Jan. 20, 2022

(65) Prior Publication Data
US 2022/0147936 A1   May 12, 2022

Related U.S. Application Data

(63) Continuation of application No. 15/616,884, filed on Jun. 7, 2017, now Pat. No. 11,232,402, which is a continuation of application No. 13/036,841, filed on Feb. 28, 2011, now abandoned.

(60) Provisional application No. 61/308,760, filed on Feb. 26, 2010.

(51) Int. Cl.
*G06Q 10/10* (2023.01)
*G16H 10/60* (2018.01)
*G16H 15/00* (2018.01)

(52) U.S. Cl.
CPC ............. *G06Q 10/10* (2013.01); *G16H 10/60* (2018.01); *G16H 15/00* (2018.01)

(58) Field of Classification Search
CPC ......... G06Q 10/10; G16H 10/60; G16H 15/00
See application file for complete search history.

(56) References Cited

U.S. PATENT DOCUMENTS

| | | | |
|---|---|---|---|
| 5,483,443 | A | 1/1996 | Milstein |
| 5,664,109 | A | 9/1997 | Johnson |
| 6,529,876 | B1 | 3/2003 | Dart |

(Continued)

FOREIGN PATENT DOCUMENTS

| | | |
|---|---|---|
| EP | 2030196 | 3/2009 |
| EP | 2030198 | 3/2009 |

(Continued)

OTHER PUBLICATIONS

Adam E.J. et al., "ESR guidelines for the communication of urgent and unexpected findings" European Society of Radiology (ESR), 2011, vol. 3, Issue (1), pp. 1-3.

(Continued)

*Primary Examiner* — Eliza A Lam
(74) *Attorney, Agent, or Firm* — Brian Bender

(57) ABSTRACT

An automated system updates electronic medical records (EMRs) based on dictated reports, without requiring manual data entry into on-screen forms. A dictated report is transcribed by an automatic speech recognizer, and facts are extracted from the report and stored in encoded form. Information from a patient's report is also stored in encoded form. The resulting encoded information from the report and EMR are reconciled with each other, and changes to be made to the EMR are identified based on the reconciliation. The identified changes are made to the EMR automatically, without requiring manual data entry into the EMR.

20 Claims, 5 Drawing Sheets

(56) References Cited

U.S. PATENT DOCUMENTS

| | | |
|---|---|---|
| 7,236,968 B2 | 6/2007 | Seki |
| 7,313,515 B2 | 12/2007 | Crouch |
| 7,379,946 B2 | 5/2008 | Carus |
| 7,650,628 B2 | 1/2010 | Zimmerman |
| 7,716,040 B2 * | 5/2010 | Koll .................. G10L 15/26 |
| | | 704/235 |
| 7,885,811 B2 | 2/2011 | Zimmerman |
| 8,050,938 B1 | 11/2011 | Green, Jr. |
| 8,452,609 B2 | 5/2013 | Berg |
| 8,706,521 B2 | 4/2014 | Ramarajan |
| 8,781,153 B2 | 7/2014 | Sharma |
| 8,781,853 B2 | 7/2014 | Green, III |
| 9,679,077 B2 | 6/2017 | Jagannathan |
| 9,704,099 B2 | 7/2017 | Koll |
| 9,996,510 B2 | 6/2018 | Koll |
| 10,156,956 B2 | 12/2018 | Koll |
| 10,325,296 B2 | 6/2019 | Koll |
| 10,877,620 B2 | 12/2020 | Koll |
| 10,950,329 B2 | 3/2021 | Koll |
| 11,043,306 B2 | 6/2021 | El |
| 2002/0029161 A1 | 3/2002 | Brodersen |
| 2002/0065854 A1 | 5/2002 | Pressly |
| 2003/0074248 A1 | 4/2003 | Braud |
| 2003/0133156 A1 | 7/2003 | Cragun |
| 2003/0154085 A1 | 8/2003 | Kelley |
| 2004/0240720 A1 | 12/2004 | Brantley |
| 2004/0243545 A1 * | 12/2004 | Boone .................. G06F 16/313 |
| 2005/0171819 A1 | 8/2005 | Keaton |
| 2005/0203775 A1 | 9/2005 | Chesbrough |
| 2006/0036472 A1 | 2/2006 | Crockett |
| 2006/0277073 A1 | 12/2006 | Heilbrunn |
| 2007/0013968 A1 | 1/2007 | Ebaugh |
| 2007/0016450 A1 | 1/2007 | Bhora |
| 2007/0016451 A1 | 1/2007 | Tilson |
| 2007/0067185 A1 | 3/2007 | Halsted |
| 2007/0143141 A1 | 6/2007 | Villasenor |
| 2007/0192143 A1 | 8/2007 | Krishnan |
| 2008/0016164 A1 | 1/2008 | Chandra |
| 2008/0028300 A1 | 1/2008 | Krieger |
| 2008/0141117 A1 | 6/2008 | King |
| 2009/0070290 A1 | 3/2009 | Nye |
| 2009/0077658 A1 | 3/2009 | King |
| 2009/0271218 A1 | 10/2009 | Mok |
| 2009/0287678 A1 | 11/2009 | Brown |
| 2010/0099974 A1 | 4/2010 | Desai |
| 2010/0100570 A1 | 4/2010 | Constantin |
| 2010/0278453 A1 | 11/2010 | King |
| 2010/0299320 A1 | 11/2010 | Claud |
| 2011/0043652 A1 | 2/2011 | King |
| 2011/0055688 A1 | 3/2011 | Isidore |
| 2011/0239146 A1 | 9/2011 | Dutta |
| 2011/0295864 A1 | 12/2011 | Betz |
| 2012/0010900 A1 | 1/2012 | Kaniadakis |
| 2012/0016690 A1 | 1/2012 | Ramarajan |
| 2013/0110547 A1 | 5/2013 | Englund |
| 2013/0159408 A1 | 6/2013 | Winn |
| 2013/0226617 A1 | 8/2013 | Mok |
| 2013/0238330 A1 | 9/2013 | Santos |
| 2014/0019128 A1 | 1/2014 | Riskin |
| 2014/0288970 A1 | 9/2014 | Lee |
| 2015/0066537 A1 | 3/2015 | Sheffer |
| 2015/0088504 A1 | 3/2015 | Jagannathan |
| 2015/0134349 A1 | 5/2015 | Vdovjak |
| 2015/0278449 A1 | 10/2015 | Laborde |
| 2015/0356198 A1 | 12/2015 | D'Souza |
| 2015/0356647 A1 | 12/2015 | Reiser |
| 2016/0093010 A1 | 3/2016 | Vasiliu-Feltes |
| 2016/0147955 A1 | 5/2016 | Shah |
| 2016/0166220 A1 | 6/2016 | Bar-Shalev |
| 2016/0179770 A1 | 6/2016 | Koll |
| 2016/0294964 A1 | 10/2016 | Brune |
| 2016/0371447 A1 | 12/2016 | Koman |
| 2017/0068781 A1 | 3/2017 | Zasowski |
| 2018/0040087 A1 | 2/2018 | Koll |
| 2018/0081859 A1 | 3/2018 | Snider |
| 2018/0101879 A1 | 4/2018 | Koll |
| 2018/0204645 A1 | 7/2018 | Saadawi |
| 2018/0276188 A1 | 9/2018 | Koll |
| 2019/0026436 A1 | 1/2019 | Bender |

FOREIGN PATENT DOCUMENTS

| | | |
|---|---|---|
| EP | 2883203 | 6/2015 |
| EP | 3571608 | 11/2019 |
| JP | 4037250 | 1/2008 |
| JP | 6215383 | 6/2013 |
| JP | 6339566 | 6/2018 |
| JP | 6388864 | 9/2018 |
| WO | WO 2005-122002 | 12/2005 |
| WO | WO 2009-143395 | 11/2009 |
| WO | WO 2012-048306 | 4/2012 |
| WO | WO 2015-079354 | 6/2015 |
| WO | WO 2015-136404 | 9/2015 |
| WO | WO 2015-187604 | 12/2015 |
| WO | WO 2018-136417 | 7/2018 |
| WO | WO 2019-103930 | 5/2019 |

OTHER PUBLICATIONS

Advisory Action dated Nov. 21, 2018 in U.S. Appl. No. 14/941,445 of Detlef Koll, filed Nov. 13, 2015, 2 pages.

Anonymous, "DMXzone Universal Form Validator PHP", Sep. 2, 2009, XP055432714,[online: https://www.dmxzone.com/Downloads/Tutorial_FormValidatorPHP_update.zip/FormValidatorPHP_update.pdf].

Arup 106428 et al., "Context-based Speech Recognition Error Detection and Correction," Proceedings of HLT-NAACL 2004: Short Papers, May 2004, 4 pages.

Centers for Medicare & Medicaid Services, "Medicare Physician Guide: 1995 Documentation Guidelines for Evaluation and Management Services," 1995, 16 pages [online: https://www.cms.gov/Outreach-and-Education/Medicare-Learning-Network-MLN/MLNEdWebGuide/Downloads/95Docguidelines.pdf].

Centers for Medicare & Medicaid Services, "Medicare Physician Guide: 1997 Documentation Guidelines for Evaluation and Management Services," 1997, 49 pages [online: https://www.cms.gov/Outreach-and-Education/Medicare-Learning-Network-MLN/MLNEdWebGuide/Downloads/97Docguidelines.pdf].

Communication pursuant to Article 94(3) EPC dated Jan. 8, 2019 by the European Patent Office in patent Application No. 13809956.9, 5 pages.

Communication Pursuant to Article 94(3) EPC, dated Jun. 27, 2019, in EPO application No. 14762803.6, 11 pages.

Daugherty B. et al., "Tracking Incidental Findings", Radiology Today, Jul. 2014, vol. 15, No. 7, p. 6.

Decision of Refusal dated Apr. 19, 2021, by the European Patent Office in patent application No. 13809956.9, 12 pages.

Decision to Refuse European Application dated Oct. 24, 2019 in European Patent Application No. 11748231.5, 19 pages.

Examination Report dated Feb. 4, 2020, in Canadian patent application No. 2,904,656, 5 pages.

Examination Report dated Jun. 18, 2019, in Canadian patent application No. 2,811,942, 6 pages.

Examination Report received in Canadian patent application No. 2,791,292 dated Mar. 9, 2020, 3 pages.

Examination Report received in Canadian patent application No. 2,791,292 dated Aug. 2, 2019, 7 pages.

Examination Report received in Canadian patent application No. 2,791,292 dated Sep. 19, 2018, 9 pages.

Examiner's Report dated Apr. 15, 2019 in Canadian patent application No. 2,875,584, 4 pages.

Examiner's Report dated Dec. 20, 2018 in Canadian patent application No. 2,839,266, 4 pages.

Examiner's Report dated Jun. 27, 2019 in Canadian Patent Application No. 2,881,564, 6 pages.

Examiner's Report dated Nov. 29, 2019 in Canadian patent application No. 2,839,266, 4 pages.

(56) References Cited

OTHER PUBLICATIONS

Exhibit 1003 of Petition for Inter Parties Review of U.S. Pat. No. 8,781,829 filed before the Patent Trial and Appeal Board on Dec. 21, 2018 by Petitioner Nuance Communications, Inc., Declaration of Andrew Sears.
Exhibit 1004 of Petition for Inter Parties Review of U.S. Pat. No. 8,781,829 filed before the Patent Trial and Appeal Board on Dec. 21, 2018 by Petitioner Nuance Communications, Inc., Curriculum Vitae of Andrew Sears.
Exhibit 1005 of Petition for Inter Parties Review of U.S. Pat. No. 8,781,829 filed before the Patent Trial and Appeal Board on Dec. 21, 2018 by Petitioner MModal Services Ltd., Michael Freeman Bliss, "Speech Recognition for Health Professionals", Pearson Prentice Hall, pp. 18-24, (2005).
Exhibit 1007 of Petition for Inter Parties Review of U.S. Pat. No. 8,781,829 filed before the Patent Trial and Appeal Board on Dec. 21, 2018 by Petitioner Nuance Communications, Inc., Panzarasa et al., "Technical Solutions for Integrating Clinical Practice Guidelines with Electronic Patient Records", pp. 141-154, (2010).
Exhibit 1009 of Petition for Inter Parties Review of U.S. Pat. No. 8,781,829 filed before the Patent Trial and Appeal Board on Dec. 21, 2018 by Petitioner Nuance Communications, Inc., Joel D. Miller and Elizabeth M. Wenzel, "Recent Developments in Slab: A Software-Based System for Interactive Spatial Sound Synthesis", Proceedings of 2002, Int'l Conf. on Auditory Display, pp. IDAC02 1-6, Jul. 2-5, 2002.
Exhibit 1010 of Petition for Inter Parties Review of U.S. Pat. No. 8,781,829 filed before the Patent Trial and Appeal Board on Dec. 21, 2018 by Petitioner MModal Services Ltd., JCAHO—Specification Manual for National Implementation of Hospital Core Measures, Version 2.0 (Mar. 1, 2004).
Exhibit 1011 of Petition for Inter Parties Review of U.S. Pat. No. 8,781,829 filed before the Patent Trial and Appeal Board on Dec. 21, 2018 by Petitioner MModal Services Ltd., JCAHO—Introduction and Background.
Exhibit 1012 of Petition for Inter Parties Review of U.S. Pat. No. 8,781,829 filed before the Patent Trial and Appeal Board on Dec. 21, 2018 by Petitioner Nuance Communications, Inc., JCAHO—Using The Specifications Manual or National Implementation of Hospital Core Measures.
Exhibit 1013 of Petition for Inter Parties Review of U.S. Pat. No. 8,412,524 filed before the Patent Trial and Appeal Board on Dec. 21, 2018 by Petitioner Nuance Communications, Inc., W. H. Auden, "Menu Selection and Form Filling", Semantic Organization, Chapter 3, 1970.
Exhibit 1014 of Petition for Inter Parties Review of U.S. Pat. No. 8,781,829 filed before the Patent Trial and Appeal Board on Dec. 21, 2018 by Petitioner MModal Services Ltd., Alan J_ Dix et al., "Human-Computer Interaction", 2nd ed., pp. 130-137, (1998).
Exhibit 1015 of Petition for Inter Parties Review of U.S. Pat. No. 8,781,829 filed before the Patent Trial and Appeal Board on Dec. 21, 2018 by Petitioner Nuance Communications, Inc., Frequently Asked Questions: Signature Requirements, Cahaba Government Benefit Administrators (Mar. 2011).
Exhibit 1016 of Petition for Inter Parties Review of U.S. Pat. No. 8,781,829 filed before the Patent Trial and Appeal Board on Dec. 21, 2018 by Petitioner Nuance Communications, Inc., WayBackMachine capture of CDC Website ICD-9-CM Classification explanation, available at https://web.archive.org/web/20110430031819/https://www.cdc.gov/nchs/icd/icd9cm.htm (Apr. 30, 2011).
Exhibit 1017 of Petition for Inter Parties Review of U.S. Pat. No. 8,781,829 filed before the Patent Trial and Appeal Board on Dec. 21, 2018 by Petitioner MModal Services Ltd., MModal's Preliminary Claim Construction Disclosure, *MModal Services Ltd v. Nuance Communications, Inc.*, Case No. 1:18-cv-00901-WMR (N.D. Ga. Dec. 3, 2018).
Exhibit 1018 of Petition for Inter Parties Review of U.S. Pat. No. 8,781,829 filed before the Patent Trial and Appeal Board on Dec. 21, 2018 by Petitioner Nuance Communications, Inc., JCAHO Facts, Joint Commission on Accreditation of Healthcare Organizations, {Aug. 1, 2005).
Exhibit 1019 of Petition for Inter Parties Review of U.S. Pat. No. 8,781,829 filed before the Patent Trial and Appeal Board on Dec. 21, 2018 by Petitioner Nuance Communications, Inc., Roe, D. B., & Wilpon, J.G. (Eds.). Voice Communication between humans and machines. National Academies Press., pp. 165-198 (1994).
Exhibit 1020 of Petition for Inter Parties Review of U.S. Pat. No. 8,781,829 filed before the Patent Trial and Appeal Board on Dec. 21, 2018 by Petitioner MModal Services Ltd., Win Phillips, "Introduction to Natural Language Processing, Consortium on Cognitive Science Instruction (Apr. 1999)", available at https://web.archive.org/web/20090221020728/http:/www.mind.1stu.edu/curriculum/protothinker/natural language orocessing_php (Sep. 1, 2006).
Exhibit 1021 of Petition for Inter Parties Review of U.S. Pat. No. 8,781,829 filed before the Patent Trial and Appeal Board on Dec. 21, 2018 by Petitioner Nuance Communications, Inc., Laurence S. Gillick, "A Rapid Match Algorithm for Continuous Speech Recognition", HLT 1990 Proceedings of the Workshop on Speech and Natural Language, pp. 170-172, (Jun. 24, 1990).
Exhibit 1022 of Petition for Inter Parties Review of U.S. Pat. No. 8,781,829 filed before the Patent Trial and Appeal Board on Dec. 21, 2018 by Petitioner Nuance Communications, Inc., Declaration of Dr. James Mullins regarding public availability of Panzarasa, pp. 1-66.
Exhibit 1022 of Petition for Inter Parties Review of U.S. Pat. No. 8,781,829 filed before the Patent Trial and Appeal Board on Dec. 21, 2018 by Petitioner MModal Services Ltd., Declaration of Dr. James Mullins regarding public availability of Panzarasa, pp. 67-110.
Exhibit 1022 of Petition for Inter Parties Review of U.S. Pat. No. 8,781,829 filed before the Patent Trial and Appeal Board on Dec. 21, 2018 by Petitioner Nuance Communications, Inc., Declaration of Dr. James Mullins regarding public availability of Panzarasa, pp. 111-153.
Exhibit 1022 of Petition for Inter Parties Review of U.S. Pat. No. 8,781,829 filed before the Patent Trial and Appeal Board on Dec. 21, 2018 by Petitioner Nuance Communications, Inc., Declaration of Dr. James Mullins regarding public availability of Panzarasa, pp. 154-201.
Exhibit 1022 of Petition for Inter Parties Review of U.S. Pat. No. 8,781,829 filed before the Patent Trial and Appeal Board on Dec. 21, 2018 by Petitioner Nuance Communications, Inc., Declaration of Dr. James Mullins regarding public availability of Panzarasa, pp. 202-243.
Exhibit 1022 of Petition for Inter Parties Review of U.S. Pat. No. 8,781,829 filed before the Patent Trial and Appeal Board on Dec. 21, 2018 by Petitioner MModal Services Ltd., Declaration of Dr. James Mullins regarding public availability of Panzarasa, pp. 244-273 end.
Extended European Search Report dated Jul. 15, 2021, in European patent application No. 18880181.5, 9 pages.
Extended European Search Report dated Sep. 25, 2020, in European patent application No. 18741689.6, 14 pages.
Final Office Action dated Sep. 4, 2018 in U.S. Appl. No. 14/218,220 of Juergen Fritsch, filed Mar. 18, 2014, 46 pages.
Final Rejection dated Jan. 21, 2021 for U.S. Appl. No. 15/993,958 of Detlef Koll, filed May 31, 2018, 21 pages.
Final Rejection dated Jul. 14, 2020 for U.S. Appl. No. 15/788,522 of Detlef Koll, filed Oct. 19, 2017, 33 pages.
Final Rejection dated Jul. 21, 2020 in U.S. Appl. No. 15/872,532 of Gilan El Saadawi, filed Jan. 16, 2018, 38 pages.
Final Rejection dated Mar. 16, 2020 for U.S. Appl. No. 15/993,958 of Detlef Koll, filed May 31, 2018, 33 pages.
Final Rejection dated Nov. 5, 2019 for U.S. Appl. No. 14/941,445 of Detlef Koll, filed Nov. 13, 2015, 19 pages.
Final Rejection dated Nov. 19, 2020 for U.S. Appl. No. 16/193,443 of Derek L. Nichols, filed Nov. 16, 2018, 42 pages.
Final Rejection dated Nov. 27, 2019 for U.S. Appl. No. 15/872,532 of Gilan El Saadawi, filed Jan. 16, 2018, 33 pages.
Final Rejection dated Oct. 11, 2018 for U.S. Appl. No. 14/941,445 of Detlef Koll, filed Nov. 13, 2015, 16 pages.
First Examination Report in Indian patent application No. 2186/MUMNP/2012 dated Jul. 19, 2019, 7 pages.

(56) References Cited

OTHER PUBLICATIONS

First Examination Report dated Aug. 29, 2019 in Indian patent application No. 448/MUMNP/2013, 6 pages.
First Examination Report dated Dec. 24, 2019, in Indian patent application No. 336/DELNP/2014, 7 pages.
First Examination Report dated Oct. 7, 2019 in Indian patent application No. 7449/DELNP/2012, 9 pages.
Hassanpour Saeed et al., "Information extraction from multi-institutional radiology reports," Artificial Intelligence in Medicine, Elsevier NL, vol. 66, Oct. 3, 2015, pp. 29-39.
International Preliminary Report on Patentability, dated Aug. 1, 2019 in International Patent Application No. PCT/US2018/013868, 9 pages.
International Search Report and Written Opinion received for PCT Patent Application No. PCT/US2018/013868, dated Jun. 18, 2018, 14 pages.
International Search Report and Written Opinion received for PCT Patent Application No. PCT/US2018/061517, dated Mar. 7, 2019, 10 pages.
James Flanagan, et al. "Defining the Standards for Automated E&M Coding Through Coding Consistency Methodology," Perspectives in Health Information Management, CAC Proceedings; Fall 2008, 7 pages [online: http://perspectives.ahima.org/defining-the-standards-for-automated-eam-coding-through-coding-consistency-methodology/].
"Medical Decision Making and the Marshfield Clinic Scoring Tool FAQ," American College of Emergency Physicians, May 24, 2017, 3 pages [online: https://www.acep.org/administration/reimbursement/reimbursement-faqs/medical-decision-making-and-the-marshfield-clinic-scoring-tool-faq/#sm.0000191uk7uslud34somv72pq17x3].
Meliha Yetisgen-Yildiz et al., "A text processing pipeline to extract recommendations from radiology reports," Journal of Biomedical Informatics, vol. 46, No. 2, Jan. 24, 2013, pp. 354-362.
Non Final Rejection dated Apr. 3, 2020 for U.S. Appl. No. 15/872,532 of Gilan El Saadawi, filed Jan. 16, 2018, 22 pages.
Non final rejection dated Apr. 12, 2021 for U.S. Appl. No. 16/193,443 of Derek L. Nichols, filed Nov. 16, 2018, 24 pages.
Non Final Rejection dated Jun. 10, 2020 for U.S. Appl. No. 15/993,958 of Detlef Koll, filed May 31, 2018, 14 pages.
Non Final Rejection dated Mar. 19, 2020 for U.S. Appl. No. 16/174,503 of Detlef Koll, filed Oct. 30, 2018, 43 pages.
Non Final Rejection dated May 14, 2020 for U.S. Appl. No. 16/193,443 of Derek L. Nichols, filed Nov. 16, 2018, 64 pages.
Non-Final Office Action dated Sep. 4, 2018 in U.S. Appl. No. 15/839,037 of Detlef Koll, filed Dec. 12, 2017, 22 pages.
Non-Final Rejection dated Jan. 9, 2020 for U.S. Appl. No. 15/788,522 of Detlef Koll, filed Oct. 19, 2017, 55 pages.
Non-Final Rejection dated Jul. 22, 2019 in U.S. Appl. No. 14/941,445 of Detlef Koll, filed Nov. 13, 2015, 29 pages.
Non-Final Rejection dated Jun. 19, 2019 in U.S. Appl. No. 15/872,532 of Gilan El Saadawi, filed Jan. 16, 2018, 54 pages.
Non-Final Rejection dated Mar. 6, 2020 in U.S. Appl. No. 14/941,445 of Detlef Koll, filed Nov. 13, 2015, 16 pages.
Non-Final Rejection dated Sep. 16, 2019 for U.S. Appl. No. 15/993,958 of Detlef Koll, filed May 31, 2018, 65 pages.
Notice of Allowance dated Mar. 9, 2021 for U.S. Appl. No. 15/872,532 of Gilan El Saadawi, filed Jan. 16, 2018, 26 pages.
Notice of Allowance dated Nov. 3, 2020 for U.S. Appl. No. 14/941,445 of Detlef Koll, filed Nov. 13, 2015, 42 pages.
Notice of Allowance dated Sep. 11, 2020 for U.S. Appl. No. 16/174,503 of Detlef Koll, filed Oct. 30, 2018, 33 pages.
OpenVPMS, Follow-up tasks, Submitted by Matt Con Fri, Sep. 17, 2010, Available at: https://openvpms.org/project/ followup-task-lists-enhancements.
Petition for Inter Parties Review of U.S. Pat. No. 8,781,829 filed before the Patent Trial and Appeal Board on Dec. 21, 2018 by Petitioner Nuance Communications, Inc., 81 pages.
Sayon Dutta et al., "Automated Detection Using Natural Language Processing of Radiologists Recommendations or Additional Imaging of Incidental Findings," Annals of Emergency Medicine, vol. 62, No. 2, Aug. 1, 2013, pp. 162-169.
Second Examiner's Report dated May 20, 2020, in Canadian patent application No. 2,875,584, 5 pages.
Slabodkin Greg, "CMS proposed rulereduces Evaluation and Management coding burden", Jul. 13, 2018, 4 pages, https://www.healthdatamanagement.com/news/cms-proposed-rule-reduces-evaluation-and-management-coding- burden?reconf=1.
Stephanie L. Jones "E/M Audit Tool: To be used with AAPC Specialty examinations," 2006 reprinted by American Academy of Professional Coders, 2 pages [online: https://c.ymcdn.com/sites/www.txosteo.org/resource/resmgr/imported/EM%20AuditTool%20from%20Practicum.pdf].
Summons to Attend Oral Proceedings Pursuant to Rule 115(1) EPC mailed Mar. 24, 2020, by the European Patent Office in patent application No. 13809956.9, 10 pages.
Summons to Attend Oral Proceedings Pursuant to Rule 115(1) EPC mailed Jun. 12, 2019 in European Patent Application No. 11748231.5, 11 pages.
Summons to Attend Oral Proceedings pursuant to Rule 115(1) EPC mailed Oct. 31, 2018, in European Patent Application No. 12802338.9, 8 pages.
Third Examiner's Report dated Apr. 22, 2021, in Canadian patent application No. 2,875,584, 4 pages.
Yildiz MY et al., "A text processing pipeline to extract recommendations from radiology reports", Journal of Biomedica informatics, 2013, vol. 46, pp. 354-362.

* cited by examiner

CLINICAL DATA RECONCILIATION AS PART OF A REPORT GENERATION SOLUTION

BACKGROUND

An Electronic Medical Record (EMR) is a database record or other data structure that is used by hospitals and other health care facilities to store current information about patients. Ideally, all information about the patient is stored within the patient's EMR, thereby eliminating the need for traditional paper files.

Within an EMR system used by a particular health care facility, each patient has his or her own EMR for storing both current and historical information about the patient. Some of the data stored within a particular EMR may be divided into discrete fields, such as a "First Name" field, a "Last Name" field, a "Date of Birth" field, "Medications," "Allergens," and so on. To store information in an EMR, the EMR system typically displays an on-screen form in which the name of each field is displayed adjacent to a blank space. A healthcare worker types the appropriate information into the blank space associated with each field. Although other user interface elements, such as checkboxes and drop-down lists, may facilitate the act of entering data into an EMR, the data entry process still essentially involves manually entering data into discrete fields in the EMR.

This process can be tedious, time-consuming, and error-prone. Despite these problems, many EMR forms are filled out correctly and completely when they are first created. More problematic is the process of keeping EMRs up to date as the information associated with the corresponding patient changes. Ideally, as a patient's diagnosis, prognosis, treatments, and personal information changes, such updated information would be entered into the patient's EMR quickly, accurately, and completely. There are, however, many barriers to updating EMRs.

For example, updated patient information may be obtained in a wide variety of settings, including those in which the healthcare worker obtaining the information does not have convenient, or any, access to a computer through which the patient's EMR may be updated. When a doctor next visits with the patient, for example, the patient may orally report to the doctor that he has stopped taking a particular medication. Although ideally the discrete data elements in the patient's EMR would be updated immediately to reflect this change in medication, doctors typically prefer to record information from a patient visit by dictating a report of the visit. The resulting transcript typically is imported into a "notes" section of the patient's EMR. The notes section typically represents the doctor's report in the form of free-form text or other unstructured data.

If information from the doctor's report is to be used to update discrete data in the patient's EMR (such as the list of the patient's medications or allergies), typically it is necessary for a person to manually review the notes, extract relevant information from them, and then enter such information into discrete data elements in the EMR using the above-mentioned on-screen form, perhaps hours or days after the patient's visit. This is a tedious, time-consuming, and error-prone way of updating the discrete data elements in the patient's EMR. In fact, the barriers raised by this method of updating discrete data elements in the patient's EMR often leads to such updates not being made at all. As a result, the patient's EMR may become increasingly out-of-date, and therefore increasingly inaccurate, over time.

What is needed, therefore, are improved techniques for updating electronic medical records.

SUMMARY

An automated system updates electronic medical records (EMRs) based on dictated reports, without requiring manual data entry into on-screen forms. A dictated report is transcribed by an automatic speech recognizer, and facts are extracted from the report and stored in encoded form. Information from a patient's report is also stored in encoded form. The resulting encoded information from the report and EMR are reconciled with each other, and changes to be made to the EMR are identified based on the reconciliation. The identified changes are made to the EMR automatically, without requiring manual data entry into the EMR.

For example, one embodiment of the present invention is directed to a computer-implemented method comprising: (1) extracting a fact from a report, wherein the fact relates to a particular concept; (2) identifying, in an electronic record, a discrete data element relating to the particular concept; (3) reconciling the extracted fact with the discrete data element; (4) updating the identified discrete data element based on the result of the reconciliation; and (5) storing text in the electronic record based on the report.

Other features and advantages of various aspects and embodiments of the present invention will become apparent from the following description and from the claims.

DETAILED DESCRIPTION

Figure 1:
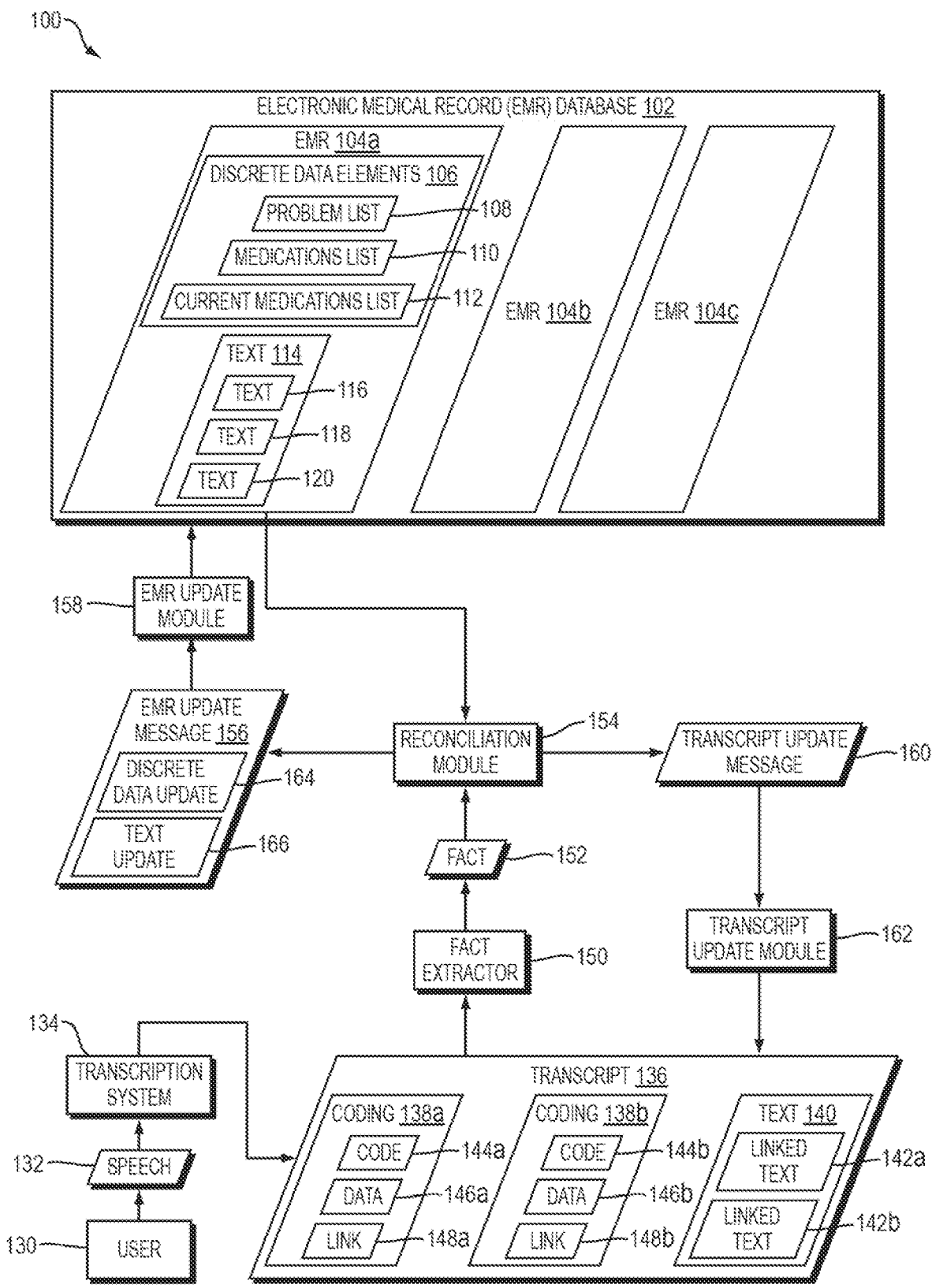
FIG. 1 is a dataflow diagram of a system for automatically updating an electronic medical record based on speech according to one embodiment of the present invention.
Figure 2:
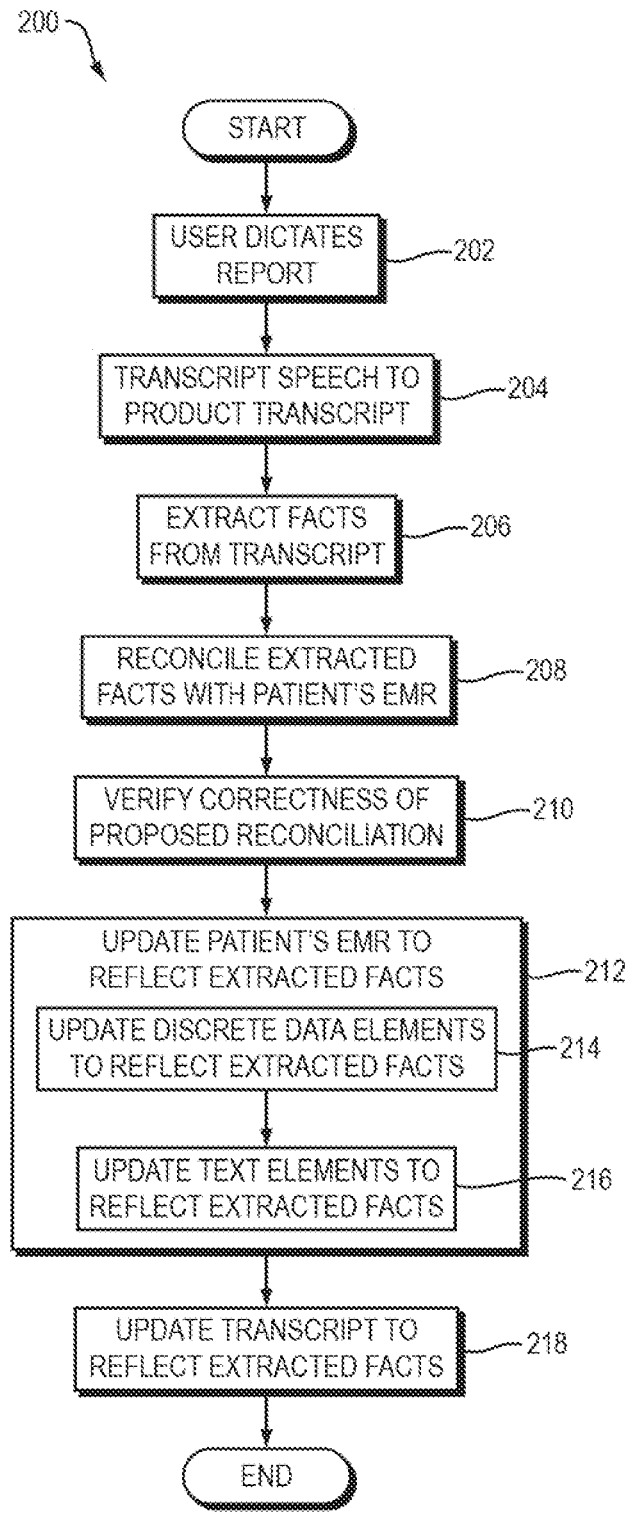
FIG. 2 is a flowchart of a method performed by the system of FIG. 1 according to one embodiment of the present invention.

Embodiments of the present invention are directed to techniques for updating electronic medical records (EMRs) quickly, accurately, and with minimal human effort. For example, FIG. 1 shows a dataflow diagram of a system 100 for automatically updating an EMR based on the content of a transcript according to one embodiment of the present invention. FIG. 2 shows a flowchart of a method performed by the system 100 of FIG. 1 according to one embodiment of the present invention.

In the system 100 of FIG. 1, an EMR database 102 contains a plurality of EMRs 104a-c, each of which may correspond to a distinct patient. For ease of illustration, only the contents of EMR 104a are shown in FIG. 1. However, EMRs 104b and 104c may contain data having the same or similar format as that shown for EMR 104a.

More specifically, EMR 104 contains both discrete data elements 106 and text 114. The discrete data elements 106 may include, for example, a problem list 108, a medications list 110, and a current medications list 112. The problem list 108 may include data representing the corresponding patient's current medical problems that are known to the system 100. The medications list 110 may include data representing all of the medications known to the system 100 that the patient currently is taking or has taken in the past. The current medications list 112 may include data representing all of the medications known to the system 100 that the patient currently is taking. This set of discrete data elements 106 is shown merely for purposes of example and does not constitute a limitation of the present invention. Embodiments of the present invention may be used with any discrete data elements.

The data elements 106 are "discrete" in the sense that they are encoded in a format that makes their meaning understandable to and processable by a computer. For example, the problem list 108 may be encoded in a way that enables a computer to understand that the data in the problem list 108 represents the corresponding patient's current problems. As a result, a computer may respond to a query which asks for the patient's current problems by providing output representing the contents of the problem list 108. Because the data in the problem list 108 are discrete, such data may be processed without parsing the problem list 108 or applying natural language processing to the problem list 108.

The EMR 104a may also include text 114. In the example shown in FIG. 1, the text 114 is shown as including separate units of text 140, 118, and 120. Such text may include any text relating to the corresponding patient. For example, such text may include transcripts of reports dictated by a doctor about the patient corresponding to EMR 104a. Text 140 may be text relating to the problem list 108, text 118 may be text relating to the medications list 110, and text 120 may be text relating to the current medications list 112. The text 114 may include text relating to the current state of the corresponding patient and/or text relating to past states of the corresponding patient. For example, each time the patient visits the hospital and the patient's doctor dictates a report about the patient, the report may be transcribed and added to the text 114 along with an indication of the date of the report.

The text 114 does not constitute "discrete" data as that term is used herein. Instead, text 114 is "free form" data. For example, the text 114 may lack codings or other information necessary to enable a computer to understand the meaning of the text 114 without parsing the text. For example, if the text 114 includes transcriptions of complete sentences spoken by a doctor, then it may not be possible to extract discrete data from such text 114 without first applying natural language processing (NLP) or other processing to the text 114, as described in more detail below. For example, if the discrete data elements 106 are encoded using XML-based encoding, the text 114 may be stored in a plain-text format or other format lacking XML tags.

Assume for purposes of example that the problem list 108 of EMR 104a indicates that the corresponding patient currently has hypertension, bipolar disorder, and a fracture of the left femur. Further assume for purposes of example that the current medications list 112 of EMR 104a indicates that the corresponding patient is currently taking Lasix and 20 mg b.i.d (i.e., twice per day) of Celexa.

Now assume that a doctor visits with this patient and observes that the patient's femur fracture has healed and that the patient stopped taking the medication Celexa in May. The doctor, represented in FIG. 1 as user 130, might then dictate the following into a digital voice recorder (FIG. 2, operation 202): "Date of visit Jun. 1, 2008 . . . . His fracture healed well. He is also feeling much better since his last visit and stopped taking Celexa around May. Current Medications: Tylenol as needed for pain."

Embodiments of the present invention may be used to update the patient's EMR 104a automatically based on the information contained in the doctor's dictated speech 132 (whether in real-time or based on an audio recording of the report), without requiring the doctor 130 or anyone else to manually enter such information into the EMR 104a using an on-screen form or any other non-speech interface.

Such automatic updating of the patient's EMR 104a may be performed as follows. The doctor's speech 132 may be transcribed by a transcription system 134 to produce a transcript 136 of the speech 132 (FIG. 2, operation 204). Note that the speech 132 may be a spoken audio stream that takes any form. For example, the speech 132 may be a live audio stream received directly or indirectly (such as over a telephone or IP connection), or an audio stream recorded on any medium and in any format.

The transcription system 134 may produce the transcript 136 using, for example, an automated speech recognizer or a combination of an automated speech recognizer and human transcriptionist. The transcription system 134 may, for example, produce the transcript 136 using any of the techniques disclosed in U.S. Pat. No. 7,584,103, issued Sep. 1, 2009, entitled, "Automated Extraction of Semantic Content and Generation of a Structured Document from Speech." As described therein, the transcript 136 may include text 140 that is either a literal (verbatim) transcript or a non-literal transcript of the speech 132. As further described therein, although the transcript 136 may be a plain text document, the transcript 136 may also, for example, in whole or in part be a structured document, such as an XML document which delineates document sections and other kinds of document structure. Various standards exist for encoding structured documents, and for annotating parts of the structured text with discrete facts (data) that are in some way related to the structured text. Examples of existing techniques for encoding medical documents include the HL7 CDA v2 XML standard (ANSI-approved since May 2005), SNOMED CT, LOINC, CPT, ICD-9 and ICD-10, and UMLS.

As shown in FIG. 1, the transcript 136 includes one or more codings 138a-b, each of which encodes a "concept" extracted from the speech 132. The term "concept" is used herein as defined in the above-referenced U.S. Pat. No. 7,584,103. Reference numeral 138 is used herein to refer generally to all of the codings within the transcript 136. Although in FIG. 1 only two codings, designated 138a and 138b, are shown, the transcript 136 may include any number of codings.

In the context of a medical report, each of the codings 138 may, for example, encode an allergy, prescription, diagnosis, or prognosis. In general, each of the codings 138 includes a code and corresponding data. For example, coding 138a includes code 144a and corresponding data 146a. Similarly, coding 138b includes code 144b and corresponding data 146b.

The code 144a may, for example, indicate the type of coding (such as whether the coding 138a represents an allergy rather than a prescription), while the data 146a may represent the value of the coding 138a (such as "penicillin" for an "allergy" type coding). Examples of techniques which may be used to generate the codings 138 from speech may be found in the above-referenced U.S. Pat. No. 7,584,103.

The transcription system 134 may rely solely on the speech 132 to produce the transcript 136. Alternatively, for example, the transcription system 134 may use both the speech 132 and the data currently stored in the patient's EMR 104a to create the transcript 136. The current data in the patient's EMR 104a may, for example, be used by the transcription system 134 as context information to interpret the speech 132 and thereby to increase the accuracy of the resulting transcript 136.

A fact extractor 150 may extract one or more facts 152 from the transcript 136 automatically, such as by using the techniques disclosed in U.S. Pat. No. 7,716,040, issued on May 11, 2010, entitled, "Verification of Extracted Data" (FIG. 2, operation 206). An example of a fact that may be extracted automatically is the fact that the patient's fracture has healed and that he has stopped taking Celexa. An extracted fact may, for example, be one of the codings 138a-b from the transcript 136, or otherwise have the same structure as the codings 138a-b in the transcript (i.e., an extracted fact may include a code, data (value), and a link). Alternatively or additionally, an extracted fact may include information not included in the codings 138a-b.

A reconciliation module may then reconcile the extracted facts 152 with corresponding facts in the EMR 104a (FIG. 2, operation 208). Such reconciliation may involve matching the concepts related to the extracted facts 152 with concepts related to the discrete data elements 106 within the EMR 104a. For example, for a particular one of the extracted facts 152, the reconciliation module 154 may identify one or more concepts to which the particular extracted fact relates. The reconciliation module 154 may then identify one or more of the discrete data elements 106 that relate to the same concept as the particular extracted fact. (For example, the reconciliation module 154 may identify a single discrete data element, from among all of the discrete data elements 106, that relates to the same concept as the particular extracted fact.)

The result is that the reconciliation module 154 has identified a pairing that includes one of the extracted facts 152 and a corresponding one of the discrete data elements 106, both of which relate to the same concept as each other. The reconciliation module 154 may identify the current values of both the extracted fact and the discrete data element within such a pairing.

As part of reconciliation 208, the reconciliation module 154 may analyze the extracted fact and corresponding discrete data element to propose a reconciled fact for storage in the EMR 104a. The proposed reconciled fact may, for example, be some or all of the extracted fact (e.g., the value of the extracted fact), some or all of the corresponding discrete data element (e.g., the current value of the discrete data element), or another fact derived from the extracted fact and/or discrete data element. For example, if the reconciliation module 154 concludes that the value of the extracted fact is correct and that the value of the corresponding discrete data element is incorrect, then the reconciliation module 154 may propose that the value of the discrete data element be replaced with the value of the extracted fact. Conversely, if the reconciliation module 154 concludes that the value of the discrete data element is correct and that the value of the corresponding extracted fact is incorrect, then the reconciliation module 154 may propose that the value of the discrete data element remain unchanged in the EMR 104a.

For example, if the discrete data element indicates that the patient has diabetes and the corresponding extracted fact indicates that the patient has uncontrolled Type II diabetes, then the reconciliation module 154 may reconcile these two facts and propose that the value of the discrete data element (diabetes) be replaced with the value of the extracted fact (uncontrolled Type II diabetes) because the value of the extracted fact is more specific than the value of the discrete data element.

As another example, if the discrete data element indicates that the patient has no known drug allergies and the corresponding extracted fact indicates that the patient has an allergy to Penicillin, then the reconciliation module 154 may reconcile these two facts and propose that the value of the discrete data element (no known drug allergies) be replaced with the value of the extracted fact (allergy to penicillin) because the value of the extracted fact is inconsistent with the value of the discrete data element, and because the extracted fact is more recent than the discrete data element. The reconciliation module 154 may therefore resolve the conflict between the value of the discrete data element and the value of the corresponding extracted fact by proposing to replace the value of the discrete data element with the value of the corresponding extracted fact.

As yet another example, the reconciliation module 154 may propose that information from the discrete data element be merged with (rather than replaced by) information from the corresponding extracted fact. For example, if the discrete data element specifies that "penicillin causes hives" and the corresponding extracted fact indicates that the patient has an "allergy to penicillin, last observed 2 years ago," the reconciliation module 154 may reconcile these two facts to propose that they be merged to update the discrete data element to indicate that the patient has a "penicillin allergy, adverse reaction: hives, last observed 2 years ago."

Although in the examples described above a single extracted fact is reconciled with a single discrete data element, these are merely examples and do not constitute limitations of the present invention. Rather, in general, reconciliation 208 is the process of merging two data states, where a data state may include any and all facts known about a patient at a time, including the sum of all facts in the transcript 136. Reconciliation 208 may include not only one-to-one reconciliation of individual discrete data elements against individual extracted facts, but also reconciliation of any number of discrete data elements against any number of extracted facts. One reason for this is that the absence of a fact in either data state may in itself be meaningful and influence the process of reconciliation 208, and such absence of a fact cannot be identified merely by performing one-to-one reconciliation.

The reconciliation proposed by the reconciliation module 154 is then verified (FIG. 2, operation 210). Such verification may, for example, be performed using any of the verification techniques disclosed in the above-referenced patent entitled, "Verification of Extracted Data." Such verification may, for example, including providing output to a human operator (whether the user 130 or another user) which represents the proposed reconciliation from the reconciliation process 208. The output may, for example, represent the modification that the reconciliation module 154 proposes to make to the EMR 104a. The output may also, for example, represent the current value of the discrete data element and/or the current value of the extracted fact. As a result, the human operator may have the opportunity to review not only the proposed modification to the EMR 104a but also the data from which the proposed modification was derived.

Verification 210 may also include receiving input from the user 130 or other human operator, indicating whether the operator agrees with the proposed reconciliation (i.e., whether to accept or reject the proposed reconciliation). If the operator disagrees with the proposed reconciliation, then the operator may further provide input indicating an alternative reconciliation to be performed. For example, if the operator disagrees with the reconciliation proposed by the reconciliation module 154, the operator may propose an alternative reconciliation by, for example, editing the proposed reconciliation, or selecting the current value of the discrete data element or the value of the extracted fact as the operator's proposed reconciliation.

Verification 210 may also include verifying the accuracy of the codings 138*a-b* and/or the text 140 in the transcript 140. If the user 130 or other operator believes that any of the text 140 is incorrect, the operator may provide input to correct such text. Similarly, if the user 130 or other operator believes that any of the codings 138*a-b* are incorrect, the operator may provide input to correct such codings.

The verification performed in operation 210 may, for example, include performing legal authentication of the report 132 and/or transcript 136. As a result, the transcript 136 may be a legally authenticated transcript.

The system 100 may then update the patient's EMR 104*a* automatically to reflect the results of the reconciliation 208 and verification 210 (FIG. 2, operation 212). For example, if the human reviewer accepted a reconciliation proposed by the reconciliation module 154, then updating 212 may include updating the EMR 104*a* to reflect the reconciliation proposed by the reconciliation module 154. If the human reviewer modified a reconciliation proposed by the reconciliation module 154, then updating 212 may including updating the EMR 104*a* to reflect the modification provided by the human reviewer. In general, the updating 212 updates data in the EMR 104*a* to reflect the reconciliation as approved by the human reviewer.

More generally, such automatic updating may include one or more of: (1) automatically updating one or more discrete data elements 106 in the EMR 104*a* (FIG. 2, operation 214); (2) automatically updating the text 114 to reflect text 140 in the transcript 136; and (3) creating a link between one or more discrete data elements 106 and the corresponding units of text 114 from which those discrete data elements were derived. For example, if a particular problem in the problem list 108 was derived from text 116, then the updating performed in operation 208 may include creating a link between the particular problem in the problem list 108 and corresponding text 116.

Any particular extracted fact may relate to a particular concept. For example, one of the extracted facts 152 may relate to the patient's fracture of the left femur, which is an example of a concept. Another one of the extracted facts may relate to a particular medication currently being taken by the patient, which is another example of a concept. As these examples illustrate, different extracted facts 152 may relate to a plurality of different concepts represented within the EMR 104*a*. A single EMR 104*a* may include discrete data elements 106 relating to a plurality of different concepts.

In this example, updating the discrete data elements 106 (FIG. 2, operation 214) may include removing the data encoding "fracture of the left femur" from the patient's problem list 108 in EMR 104*a*, and removing the data encoding Celexa from the patient's current medications list 112 in EMR 104*a*.

Operations other than removing data may be performed on the discrete data elements 106 as part of updating the discrete data elements 106 in operation 214. For example, if an existing value of a discrete data element indicates that the patient has an acute problem, and a significant amount of time has passed (e.g., an amount of time exceeding some predetermined threshold, such as one month, six months, or one year) since the acute problem was recorded in the EMR 104*a* and the time at which the report 132 was dictated, and if the dictated report 132 does not explicitly indicate the current status of the problem, then the reconciliation module 154 may draw the conclusion (in reconciliation 208) that the problem is now chronic instead of acute. If this conclusion is verified (approved) by the human reviewer during verification 210, then the reconciliation module 154 may, as part of operation 214, change the status of the problem from acute to chronic.

As another example, consider a problem that is recorded in the problem list 108 without any qualifications. For example, assume that the problem "diabetes" is recorded in the problem list 108. If the report 132 indicates that the patient has type II diabetes, the reconciliation module 154 may, as part of operation 214, update the record of the problem in the problem list 108 to further specify that the patient's diabetes is of Type II (assuming that this modification was approved by the human reviewer during verification 210).

Updating the text 114 (FIG. 2, operation 216) may include one or more of: (1) storing some or all of the text 140 from the transcript 136 in the text 114 of the EMR 104*a*; (2) modifying some or all of the existing text 114 in the EMR 104*a* based on text 140 from the transcript 136; and (3) deleting some or all of the existing text 114 of the EMR 104*a*.

Such automatic identification of facts 152 from the dictated report 132 and subsequent automatic updating of the patient's EMR 104*a* to reflect those facts 152 eliminates the need for the dictating doctor 130, or any other person, to engage in a separate step of editing the EMR 104*a* directly. Instead, the acts of dictating the speech 132, reconciling the speech 132 with the data in the EMR 104*a*, and verifying the accuracy of the extracted facts 152 triggers and enables the automatic updating of both the discrete data elements 106 and the text 114 in the EMR 104*a*, without the need for any separate manual action to update the discrete data elements 106. In other words, the same act of dictation that is used to automatically populate the text 114 in the EMR 104*a* may also be used to automatically update the discrete data elements 106 in the EMR 104*a*.

One benefit of such a system is that it enables physicians and others who dictate reports to continue using dictation to enter data into EMRs, without losing the benefit of having up-to-date discrete data elements in those EMRs. Most doctors prefer to make records of their patient visits by dictating reports of such visits. Embodiments of the present invention enable discrete data elements in patient EMRs to be updated automatically without requiring doctors to enter data into such discrete elements manually, or otherwise to change their preferred modality of data entry: dictation.

More specifically, a reconciliation module 154 may use the extracted facts 152 to create a message that indicates the updated patient information. Such a message may, for example, specify one or more changes to be made to the existing (or last known) state of the patient's EMR 104*a*. The message may then be processed to automatically apply each of the specified changes to the patient's EMR 104*a*.

This message, referred to generically herein as an update message, may be generated in any of a variety of ways. In general, a state update message may be generated by reconciling: (1) the transcript 136 and/or the extracted facts 152 with (2) the existing data contained in the patient's EMR 104a (i.e., the data existing in the patient's EMR prior to dictation of the speech 132).

For example, the discrete data elements 106 in the EMR 104a may be encoded in a format such as SNOMED. The codings 138a-b in the transcript 136, and the facts 152 extracted from the transcript 136, may also be encoded in the same or different format as that used to encode the discrete data elements 106. The reconciliation module 154 may perform the reconciliation by comparing the encoded extracted facts 152 and/or codings 138a-b with the encoded discrete data elements 106. The reconciliation is facilitated by the fact that both sets of data are in encoded form (potentially in the same encoded form as each other). The reconciliation may apply ontology-based reasoning to what is known about the patient (from the patient's EMR 104a) and to the new knowledge represented by the extracted facts 152.

Consider, for example, a case in which the patient's existing problem list 108 indicates that the patient was last known to have the following problems: hypertension, bipolar disorder, and a fracture of the left femur. Further assume that the patient's existing current medications list 112 indicates that the patient was last known to be taking 20 mg b.i.d. of Celexa since Dec. 12, 2007, and that the patient was last known to be taking Lasix since Jan. 1, 2008.

Now assume that, after visiting with the patient, the doctor 130 dictates the following report: "Date of visit Jun. 1, 2008 . . . . His fracture healed well. He is also feeling much better since his last visit and stopped taking Celexa around May. Current medications: Tylenol as needed for pain." The techniques disclosed above may be used to extract the following facts 152 from this dictation: (1) resolved problem: fracture; (2) discontinued medication: Celexa, end date May 2008; (3) current medications: Tylenol.

In this example, the system 100 may automatically encode the extracted facts 152 and apply the knowledge gained from the extracted facts by updating the information (discrete data elements 106 and/or text 114) in the patient's EMR 104a to reflect the extracted facts 152 (upon approval of such modifications by the human reviewer during verification 210). For example, the system 100 may update the EMR 104a to reflect the extracted facts 152 by:

removing the indication that the patient has a fracture of the left femur from the patient's problem list 108 (or by changing the status of "fracture of the left femur" to "resolved" within the problem list 108);

removing Celexa from the patient's current medications list 112 (and indicating, in the patient's medications list 110 that the end date associated with Celexa is May 2008); and adding Tylenol to the patient's current medications list 112 (and indicating, in the patient's current medications list 112, that the start date associated with Tylenol is approximately Jun. 1, 2008).

Updating of the discrete data elements 106 and/or text 114 in the EMR 104a may be effectuated by the reconciliation module 154 creating an EMR update message 156 (after both reconciliation 208 and verification 210) indicating the updates that need to be made to the EMR 104a to cause the EMR 104a to reflect the extracted facts 152. The EMR update message 156 may include a discrete data update message 164 (indicating updates to one or more of the discrete data elements 106) and/or a text update message 166 (indicating updates to one or more of the text elements 114). An EMR update module 158 may then apply the updates specified by the EMR update message 156 to the EMR 104a.

As the examples above illustrate, embodiments of the present invention address and eliminate various problems associated with conventional techniques for updating EMRS. In particular, the embodiments described above enable the physician 130 to update both discrete data elements 106 and text 114 in the EMR 104a simply by dictating the report 132. The physician 130 need not change the manner in which the report 132 is dictated or use a graphical or textual user interface to input data into the EMR 104a. Furthermore, the physician 130 need not specify the discrete data elements to be updated. Instead, the system 100 takes on the burden of extracting facts 152 from the dictated report 132, of identifying the discrete data elements 106 corresponding to those facts in the EMR 104a, and of making appropriate changes to those facts in the EMR 104a to reflect the facts 152 extracted from the speech 132. As a result, the EMR 104a may be updated automatically and without imposing any additional burden on the doctor 130 or other staff.

Furthermore, the system 100 may update both the discrete data elements 106 and the text 114 in the EMR 104a based on the single audio stream 132 dictated by the physician 130. For example, the audio stream 132 may be transcribed (e.g., by an automatic speech recognizer) into the transcript 136, and the same transcript 136 that is used to automatically generate the extracted facts 152 and hence to update the discrete data elements 106 in the EMR 104a may also be used to automatically populate the text 114 in the EMR 104a. This eliminates the need to engage in separate, possibly manual, steps to update the discrete data elements 106 and the text 114. Furthermore, this process reduces the likelihood that discrepancies will exist between the discrete data elements 106 and the text 114 in the EMR 104a.

Similarly, the reconciliation process may include updating the transcript 136 to reflect extracted facts 152 (FIG. 2, operation 218). For example, if the facts 152 indicate that the patient is currently taking a medication and the transcript 136 contains inconsistent information about whether the patient currently is taking the medication, the transcript 136 may be updated (upon verification and approval from the physician 130) so that it contains consistent information indicating that the patient currently is taking the medication. Updating of the transcript 136 may be effectuated by the reconciliation module 154 creating a transcript update message 160 indicating the updates that need to be made to the transcript 136 to cause the transcript 136 to reflect the extracted facts 152. A transcript update module 162 may then apply the updates specified by the transcript update message 160 to the transcript 136.

Figure 3:
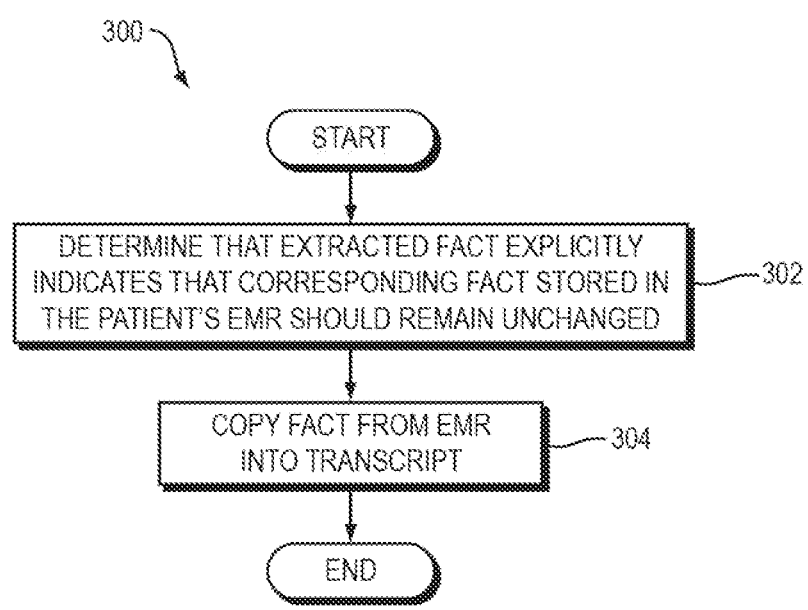
FIG. 3 is a flowchart of a method for incorporating content of an electronic medical record into a transcript based on a spoken reference to that content according to one embodiment of the present invention.

As illustrated by the method 300 of FIG. 3, another example of a way in which the transcript 136 may be updated automatically is as follows. Consider the case in which the dictated report 132 explicitly states that a particular fact stored in the EMR 104a should remain unchanged. An example of this would be one in which the report 132 includes the phrase, "allergies unchanged." The reconciliation module 154 may recognize that such a statement refers to a fact represented in the EMR 104a, and that such a statement indicates that the fact represented in the EMR 104a remains valid and unchanged (FIG. 3, operation 302). In response, the reconciliation module 154 may copy the contents of the corresponding fact(s) stored in the EMR 104a (e.g., the patient's allergy list in this example) into the transcript 136 by transmitting an appropriate transcript update message 160 to the transcript updater 162 (FIG. 3, operation 304). This feature enables the physician 130 to quickly and easily copy existing patient state information into the current report 136 by making an oral reference to such state information, thereby saving the time and effort needed to re-dictate such information, and eliminating the possibility that such information will be re-dictated or otherwise re-entered inaccurately.

In the example described above, recall that Lasix is currently on the patient's current medications list 112, yet the doctor's dictated report 132 does not make any mention of Lasix. Therefore it is unclear, based on the doctor's report 132, whether the doctor omitted Lasix from the report 132 because the patient no longer is taking Lasix, because there has been no change in the patient's use of Lasix, or for some other reason.

This is one example of an ambiguity that may exist in the report 132. In general, an ambiguity exists when a fact encoded in the patient's EMR 104a is not explicitly represented in the facts 152 extracted from the dictated report 132. For example, an ambiguity exists if the facts 152 do not indicate the current status of a problem in the problem list 108, a medication in the medications list 110, or a medication in the current medications list 112.

If a particular fact in the EMR 104a is to remain unchanged, then the EMR update message 156 may explicitly indicate that such a fact is to remain unchanged. For example, if the report 132 says, "no change in patient's use of Lasix," then the EMR update message 156 may indicate a "no change" state update for the record for Lasix in the current medications list 112. In response to such an explicit "no change" message, the "last reviewed" date of the fact in the EMR 104a may be changed to be equal to the current date. If such explicit "no change" messages are used, then an ambiguity may exist with respect to a particular fact in the EMR 104a if the EMR update message 156 does not include such a "no change" message for that fact.

Figure 4:
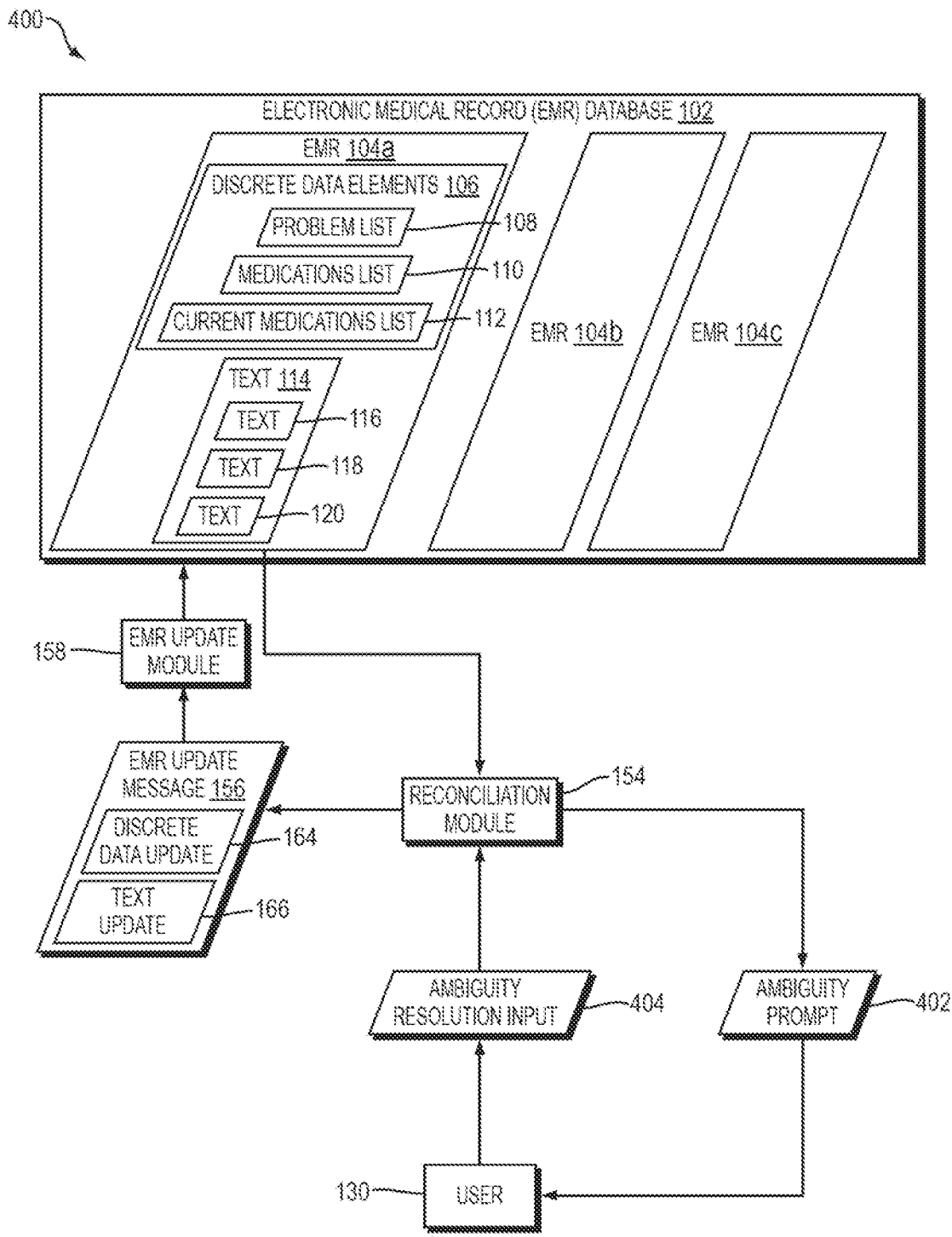
FIG. 4 is a dataflow diagram of a system for automatically identifying ambiguities in a spoken report based on the content of an electronic medical record and for resolving such ambiguities according to one embodiment of the present invention.
Figure 5:
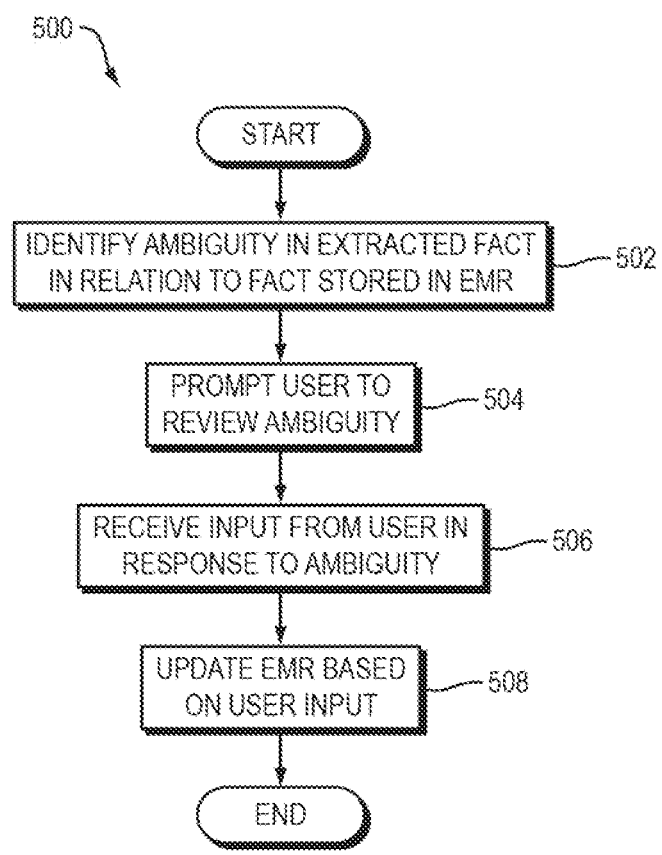
FIG. 5 is a flowchart of a method performed by the system of FIG. 4 according to one embodiment of the present invention.

The system 100 may automatically identify ambiguities such as those described above, as illustrated by the system 400 of FIG. 4 and the method 500 of FIG. 5. Although certain elements of the system 100 of FIG. 1 are not shown in FIG. 4 for ease of illustration, the system 400 of FIG. 4 may include any and all elements of the system 100 of FIG. 1 in addition to the elements shown in FIG. 4.

In response to identifying an ambiguity of one or more of the extracted facts 152 with respect to a particular fact in the EMR 104a (FIG. 5, operation 502), the system 400 may flag the fact in the EMR 104a representing the patient's current use of Lasix for manual review by the dictating physician 130 in light of the ambiguity. The system 400 may provide the physician 130 with a prompt 402 to perform such a review (FIG. 5, operation 504). In response to such a prompt, the physician 130 may manually provide input 404 representing the status of Lasix as a current medication for the patient (FIG. 5, operation 506). Such input 404 may, for example, indicate that the patient is no longer taking Lasix, that the patient still is taking Lasix as previously prescribed, or that the patient is taking Lasix at a new dosage (in which case the dosage in the EMR 104a may be updated based on the physician's input). In cases in which the system 400 prompts the physician 130 to provide such manual input 404, the system 400 may require the physician 130 to provide such input before signing off on the written report 136. In any case, the system 400 may update the EMR 104a to reflect the physician's input 404, such as by storing a record of the physician's input 404 in the EMR 104a or by updating one or more discrete data elements 106 in the EMR 104a based on the physician's input 404 (FIG. 5, operation 508).

The system 400 need not prompt the user 130 in response to all ambiguities detected by the system 400. Rather, for example, the system 400 may only prompt the user 130 in response to ambiguities satisfying some predetermined criterion or criteria. For example, a problem on the problem list 108 may be either acute or chronic, and/or either active or inactive. For example, a particular problem on the problem list 108 may be acute and active, or acute and inactive, or chronic and active, or chronic and inactive. The system 400 may be configured to prompt the user 130 to review, for example, only ambiguities related to active problems, or only ambiguities related to acute and active problems. As a result, the system 400 may not prompt the user 130 to review ambiguities related to inactive problems, or ambiguities related to acute and inactive, chronic and active, or chronic and inactive problems. Both chronic-acute and active-inactive are examples of a type of "status" as that term is used herein. Therefore, in general the system 400 may be configured to only prompt the user 130 in connection with ambiguities relating to discrete data element statuses that satisfy predetermined criteria.

The system 400 may also take action in response to other kinds of ambiguities which the system 400 identifies based on the current state of the EMR 104a and the doctor's dictation 130. For example, in the situation described above, the doctor 130 stated that "his fracture healed well." This statement is ambiguous, because it is not entirely clear whether "his fracture" refers to the fracture of the left femur currently specified in the patient's EMR 104a, or to a different fracture not currently specified in the patient's EMR 104a. The system 400 may automatically identify such an ambiguity in a variety of ways. For example, if a condition or other fact represented within the EMR 104a contains data representing qualifiers—such as "left" or "right," a date of occurrence or observation, further specific details (such as "Type II" for the problem "diabetes"), a cause-effect relationship (such as a symptom-diagnosis relationship), or an object (such as "left femur," which is the object of "fracture" in the above example)—and the corresponding fact 152 extracted from the dictated report 132 lacks all of the qualifiers stored in the EMR 104a, then the system 400 may conclude that the extracted fact 152 is ambiguous with respect to the fact stored in the EMR 104a.

In response to identifying such an ambiguity, the system 400 may flag the ambiguity for subsequent review and approval by the physician 130 in any of the ways disclosed above, such as in any of the ways disclosed in the above-referenced patent entitled, "Verification of Extracted Data." Once the physician 130 resolves the ambiguity, the system 400 may update the patient's EMR 104a based on the additional input 404 provided by the physician 130, without requiring the physician 130 to edit the EMR 104a manually.

During these and any other stages involving manual review by the physician 130 or other person, the system 400 may display a variety of information to the user 130 to assist in the review process. For example, the system 400 may display, in whole or in part, the transcript 136 (in structured or unstructured form) and/or the EMR 104a. The system 400 may display both the transcript 136 and a summary of the EMR 104a (where the summary may be a subset of or otherwise be derived from the discrete data elements 106 in the EMR 104a), such as in a side-by-side display, or in a single display in which information from the transcript 136 and EMR 104a are interleaved with each other, and in which a visual indication is provided of which information belongs to the transcript 136 and which information belongs to the EMR 104*a* (such as by using different colors or fonts). The visual display may also distinguish between current information, proposed changes to information, and accepted changes to information, such as by using different colors, fonts, or text formatting (e.g., boldface, underlining, italics, strikethrough).

Although the process disclosed above may be performed entirely automatically, such a process is still useful even when parts of it involve manual intervention. For example, even in the absence of ambiguities in the doctor's dictation, the resulting changes intended to be applied to the patient's EMR 104*a* may first be presented to the doctor 130 or other person for review and approval before being applied to the patient's EMR 104*a*. This still represents an improvement over the current state of the art, in part because it still eliminates or reduces the need for a person to perform manual data entry into an EMR form. For example, the system 100 may present the proposed changes to the doctor 130, such as by displaying "Mark 'fracture of the left femur' as 'resolved'?," thereby enabling the doctor to approve of such a change merely by typing "Y" or clicking on a single button rather than performing manual data entry operations in an EMR database system. Although in some cases it might be desirable or necessary for the doctor 130 to type certain information into the system 100, such as the name of a current medication, even this would represent an improvement over the current state of the art because the system 100 would automatically enter the doctor's response into the appropriate field in the EMR 104*a*, thereby saving the doctor's time and eliminating the possibility of the doctor 130 entering the data into the wrong field.

Once the physician 130 has signed off on the changes indicated in the reconciliation process, the system 100 may provide output representing the updated EMR 104*a*, including output representing the updated text 114 and updated discrete data elements 106.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

The techniques disclosed herein are not limited to use in connection with any particular EMR system, or in connection with any particular EMR data. The particular EMR data elements disclosed herein are merely examples and do not constitute limitations of the present invention. Other EMR data elements include, but are not limited to, current and historical medication lists, allergies, and current and historical medical problems.

The techniques disclosed herein may be integrated into an EMR system and/or work by communicating with an EMR system. In the latter case, data may, for example, be transferred from the EMR system to a system implementing the techniques disclosed herein using an ASTM Continuity of Care Record (CCR) or an HL7 CDA Continuity of Care Document (CCD).

Furthermore, although in certain examples disclosed herein, EMRs are updated automatically based on speech, the techniques disclosed herein may be applied not only to speech but also to text and other unstructured data. For example, the techniques disclosed herein may be used to extract facts from a written medical report written in prose form, and to use the extracted facts to update an EMR automatically, without the need to enter data manually into a database form.

The techniques described above may be implemented, for example, in hardware, software tangibly embodied in a computer-readable medium, firmware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices.

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in non-transitory signals in a machine-readable storage device for execution by a computer processor. Method steps of the invention may be performed by a computer processor executing a program tangibly embodied on a computer-readable medium to perform functions of the invention by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

The invention claimed is:

1. A method performed by at least one computer processor executing computer program instructions stored on at least one non-transitory computer-readable medium, wherein the computer program instructions are executable by the at least one computer processor to perform a method, the method comprising:
   (A) receiving a spoken audio stream representing speech of a user;
   (B) automatically transcribing the spoken audio stream using an automated speech recognizer to produce a document that includes the speech; and (C) automatically updating an electronic medical record (EMR) stored in a non-transitory computer readable medium, based on the document, the automatically updating comprising:
- (C)(1) automatically extracting a fact, relating to a concept, from the document;
- (C)(2) identifying a discrete data element in the EMR;
- (C)(3) automatically extracting a fact, relating to the concept, from the discrete data element;
- (C)(4) generating, based on the fact from the document and the fact from the discrete data element, a reconciled fact; and
- (C)(5) automatically generating a link between the discrete data element and text from which that discrete data element is derived, wherein (C) is performed more than once to link more than one discrete data element to a plurality of different concepts; and
- (C)(6) automatically updating a problem list based on the link, wherein (C) is performed more than once to automatically generate a plurality of links between more than one discrete data element and a plurality of different concepts.

2. The method of claim 1, wherein the document includes plain text, and wherein (C)(1) comprises automatically extracting the fact from the plain text.

3. The method of claim 1, wherein the document includes structured text, and wherein (C)(1) comprises automatically extracting the fact from the structured text.

4. The method of claim 1, wherein (C)(4) comprises:
- (C)(4)(a) determining that the fact extracted from the document is correct and that the fact extracted from the discrete element is incorrect; and
- (C)(4)(b) in response to the determination of (C)(4)(a), generating a reconciled fact based on the fact extracted from the document.

5. The method of claim 4, wherein (C)(5) comprises automatically replacing the fact in the discrete data element with the fact extracted from the document.

6. The method of claim 1, further comprising:
- (D) automatically updating free-form text contained in the EMR based on text contained in the document.

7. The method of claim 6, wherein (D) comprises replacing the free-form text contained in the EMR with the text contained in the document.

8. The method of claim 6, wherein (D) comprises storing, in the EMR, the text contained in the document.

9. The method of claim 1, wherein (C)(5) comprises:
- (C)(5)(a) sending an EMR update message, indicating the reconciled fact, to an EMR system.

10. The method of claim 9, wherein (C)(5) further comprises:
- (C)(5)(b) at the EMR system, receiving the EMR update message;
- (C)(5)(c) at the EMR system, automatically updating the EMR based on the EMR update message.

11. A non-transitory computer-readable medium containing computer program instructions, wherein the computer program instructions are executable by the at least one computer processor to perform a method, the method comprising:
- (A) receiving a spoken audio stream representing speech of a user;
- (B) automatically transcribing the spoken audio stream using an automated speech recognizer to produce a document that includes the speech; and
- (C) automatically updating an electronic medical record (EMR) stored in a non-transitory computer readable medium, based on the document, the automatically updating comprising:
  - (C)(1) automatically extracting a fact, relating to a concept, from the document;
  - (C)(2) identifying a discrete data element in the EMR;
  - (C)(3) automatically extracting a fact, relating to the concept, from the discrete data element;
  - (C)(4) generating, based on the fact from the document and the fact from the discrete data element, a reconciled fact;
  - (C)(5) automatically generating a link between the discrete data element and text from which that discrete data element is derived; and
  - (C)(6) automatically updating a problem list based on the link, wherein (C) is performed more than once to automatically generate a plurality of links between more than one discrete data element and a plurality of different concepts.

12. The non-transitory computer-readable medium method of claim 11, wherein the document includes plain text, and wherein (C)(1) comprises automatically extracting the fact from the plain text.

13. The non-transitory computer-readable medium of claim 11, wherein the document includes structured text, and wherein (C)(1) comprises automatically extracting the fact from the structured text.

14. The non-transitory computer-readable medium of claim 11, wherein (C)(4) comprises:
- (C)(4)(a) determining that the fact extracted from the document is correct and that the fact extracted from the discrete element is incorrect; and
- (C)(4)(b) in response to the determination of (C)(4)(a), generating a reconciled fact based on the fact extracted from the document.

15. The non-transitory computer-readable medium of claim 14, wherein (C)(5) comprises automatically replacing the fact in the discrete data element with the fact extracted from the document.

16. The non-transitory computer-readable medium of claim 11, wherein the method further comprises:
- (D) automatically updating free-form text contained in the EMR based on text contained in the document.

17. The non-transitory computer-readable medium of claim 16, wherein (D) comprises replacing the free-form text contained in the EMR with the text contained in the document.

18. The non-transitory computer-readable medium of claim 16, wherein (D) comprises storing, in the EMR, the text contained in the document.

19. The non-transitory computer-readable medium of claim 11, wherein (C)(5) comprises:
- (C)(5)(*a*) sending an EMR update message, indicating the reconciled fact, to an EMR system.

20. The non-transitory computer-readable medium of claim 19, wherein (C)(5) further comprises:
- (C)(5)(b) at the EMR system, receiving the EMR update message;
- (C)(5)(c) at the EMR system, automatically updating the EMR based on the EMR update message.

* * * * *